US010842880B2

(12) United States Patent
Vestberg

(10) Patent No.: US 10,842,880 B2
(45) Date of Patent: Nov. 24, 2020

(54) IMMOBILISED BIOLOGICAL ENTITIES

(71) Applicant: Carmeda AB, Upplands Väsby (SE)

(72) Inventor: Robert Vestberg, Upplands Väsby (SE)

(73) Assignee: Carmeda AB, Upplands Väsby (SE)

( * ) Notice: Subject to any disclaimer, the term of this patent is extended or adjusted under 35 U.S.C. 154(b) by 0 days.

(21) Appl. No.: 15/798,215

(22) Filed: Oct. 30, 2017

(65) Prior Publication Data

US 2018/0140713 A1 May 24, 2018

Related U.S. Application Data

(60) Continuation of application No. 13/911,727, filed on Jun. 6, 2013, now Pat. No. 10,016,512, which is a division of application No. 13/045,769, filed on Mar. 11, 2011, now Pat. No. 8,501,212.

(30) Foreign Application Priority Data

Mar. 12, 2010 (GB) .................................. 1004101.0

(51) Int. Cl.
A61K 47/61 (2017.01)
A61L 33/00 (2006.01)
A61K 47/58 (2017.01)
A61K 47/59 (2017.01)
A61K 47/69 (2017.01)

(52) U.S. Cl.
CPC .............. A61K 47/61 (2017.08); A61K 47/58 (2017.08); A61K 47/59 (2017.08); A61K 47/6957 (2017.08); A61L 33/0029 (2013.01)

(58) Field of Classification Search
CPC ........ A61K 47/58; A61K 47/59; A61K 47/61; A61K 47/6957; A61K 31/727
See application file for complete search history.

(56) References Cited

U.S. PATENT DOCUMENTS

| 3,852,253 | A | * | 12/1974 | Malatesta | .................. | C08F 8/26 |
| | | | | | | 525/332.3 |
| 4,613,665 | A | | 9/1986 | Larm | | |
| 5,049,403 | A | | 9/1991 | Larm et al. | | |
| 5,213,898 | A | | 5/1993 | Larm et al. | | |
| 6,200,955 | B1 | | 3/2001 | Harris et al. | | |
| 6,461,665 | B1 | | 10/2002 | Scholander | | |
| 6,475,495 | B1 | | 11/2002 | Maignan et al. | | |
| 6,653,457 | B1 | | 11/2003 | Larm et al. | | |
| 7,375,234 | B2 | | 5/2008 | Sharpless et al. | | |
| 8,153,268 | B1 | * | 4/2012 | Fay | ....................... | C08G 18/289 |
| | | | | | | 428/448 |
| 8,501,212 | B2 | | 8/2013 | Vestberg | | |
| 10,016,512 | B2 | | 7/2018 | Vestberg | | |
| 2002/0068183 | A1 | * | 6/2002 | Huang | ................. | A61L 33/0029 |
| | | | | | | 428/474.4 |
| 2003/0125799 | A1 | * | 7/2003 | Limon | ...................... | A61F 2/91 |
| | | | | | | 623/1.15 |
| 2004/0115151 | A1 | | 6/2004 | Giroud | | |
| 2004/0170752 | A1 | | 9/2004 | Luthra et al. | | |
| 2004/0234575 | A1 | | 11/2004 | Horres et al. | | |
| 2005/0032081 | A1 | | 2/2005 | Ju et al. | | |
| 2005/0059068 | A1 | | 3/2005 | Huang et al. | | |
| 2005/0222427 | A1 | | 10/2005 | Sharpless et al. | | |
| 2005/0266038 | A1 | * | 12/2005 | Glauser | .................. | A61L 31/10 |
| | | | | | | 424/423 |
| 2007/0020620 | A1 | | 1/2007 | Finn et al. | | |
| 2007/0154521 | A1 | | 7/2007 | Zhao | | |
| 2007/0264308 | A1 | | 11/2007 | Cleek et al. | | |
| 2008/0089919 | A1 | | 4/2008 | Cleek et al. | | |
| 2008/0311412 | A1 | | 12/2008 | Fokin et al. | | |
| 2009/0018646 | A1 | * | 1/2009 | Zhao | ....................... | A61L 31/10 |
| | | | | | | 623/1.43 |
| 2010/0074938 | A1 | | 3/2010 | Oscarson et al. | | |
| 2011/0223229 | A1 | | 9/2011 | Vestberg | | |
| 2016/0228572 | A9 | | 8/2016 | Vestberg | | |

FOREIGN PATENT DOCUMENTS

| CN | 101649011 A | 2/2010 |
| DE | 19604173 A1 | 8/1997 |
| EP | 0086186 A1 | 8/1983 |
| EP | 0086187 A1 | 8/1983 |
| EP | 0495820 A1 | 7/1992 |
| EP | 1806373 A2 | 7/2007 |
| EP | 2014308 A2 | 1/2009 |
| FR | 2920436 A1 | 3/2009 |
| JP | 03-188868 A | 8/1991 |
| JP | 3188868 B2 | 7/2001 |
| JP | 2003507082 A | 2/2003 |
| JP | 2004137274 A | 5/2004 |
| JP | 2004189627 A | 7/2004 |

(Continued)

OTHER PUBLICATIONS

Fry, "Synthesis and Anticoagulant function of Heparin Containing Block Copolymers on Polystyrene Microspheres," Master of Science thesis, 2008, 60 pages.
Miura et al., "The Self-Assembled Monolayer of Saccharide via Click Chemistry: Formation and Protein Recognition," Thin Solid Films, 2008, vol. 516, Issue 9, pp. 2443-2449.
Jones et al., "Phosphine-Mediated One-Pot Thiol-Ene 'click' approach to Polymer-Protein Conjugates," Chemical Communications, 2009, pp. 5272-5274.
Pasche et al., "Binding of Antithrombin to Immobilized Heparin Under Varying Flow Conditions," Artificial Organs, 1991, vol. 15, pp. 481-491.
Nie et al., "Production of Heparin-Containing Hydrogels for Modulating Cell Responses," Acta Biomaterialia, 2009, vol. 5, Issue 3, pp. 865-875.
Lih et al., "An In Situ Gel-Forming Heparin-Conjugated PLGA-PEG-PLGA Copolymer," Journal of Bioactive and Compatible Polymers, 2008, vol. 23, Issue 5, pp. 444-457.

(Continued)

Primary Examiner — Michael B. Pallay

(57) ABSTRACT

There is described inter alia a medical device having a surface which comprises a coating layer, said coating layer being a biocompatible composition comprising an anti-coagulant entity capable of interacting with mammalian blood to prevent coagulation or thrombus formation, which anti-coagulant entity is covalently attached to said surface through a linker comprising a thioether.

8 Claims, 7 Drawing Sheets

(56) References Cited

FOREIGN PATENT DOCUMENTS

| | | |
|---|---|---|
| JP | 2004189724 A | 7/2004 |
| JP | 2008500104 A1 | 1/2008 |
| JP | 2011092491 A | 5/2011 |
| WO | 02/34312 A1 | 5/2002 |
| WO | 03/024897 A2 | 3/2003 |
| WO | 2004/055160 A2 | 7/2004 |
| WO | 20055118018 A1 | 12/2005 |
| WO | 2006/012569 A1 | 2/2006 |
| WO | 2007/003054 A1 | 1/2007 |
| WO | 2007/011696 A2 | 1/2007 |
| WO | 2007/035296 A2 | 3/2007 |
| WO | 2008/019450 A1 | 2/2008 |
| WO | 2008/031525 A1 | 3/2008 |
| WO | 2008/090555 A2 | 7/2008 |
| WO | 2009/027454 A2 | 3/2009 |
| WO | 2009064372 A2 | 5/2009 |
| WO | 2010/065958 A1 | 6/2010 |

OTHER PUBLICATIONS

Kristensen et al., "Characterization of Heparin Surfaces using Photoelectron Spectroscopy and Quartz Crystal Microbalance," Biomaterials, 2003, vol. 24, Issue 23, pp. 4153-4159.

Jing et al., "Preparation and Characterization of Heparin-Modified Gold Nanoparticles," Journal of Clinical Rehabilitative Tissue Engineering Research, 2009; vol. 13, No. 8, pp. 1521-1524.

Iha et al., "Applications of Orthogonal 'Click' Chemistries in the Synthesis of Functional Soft Materials," Chemical Reviews, 2009, vol. 109, Issue 11, pp. 5620-5686.

Baskin et al., "Bioorthogonal Click Chemistry: Covalent Labeling in Living Systems," QSAR & Combinatorial Science, 2007, vol. 26, Issue 11-12, pp. 1211-1219.

Wilkinson et al., "Synthetic Utility of Glycosyl Triazoles in Carbohydrate Chemistry," Tetrahedron, 2006, vol. 62, Issue 34, pp. 8115-8125.

Sun et al., "Carbohydrate and Protein Immobilization onto Solid Surfaces by Sequential Diels-Alder and Azide-Alkyne Cycloadditions," Bioconjugate Chemistry, 2006, vol. 17, pp. 52-57.

Hotha et al., "'Click Chemistry' Inspired Synthesis of pseudo-Oligosaccharides and Amino Acid Glycoconjugates," The Journal of Organic Chemistry, 2006, vol. 71, pp. 364-367.

Dedola et al., "Recent application of the CU(I)-catalysed Huisgen azide-alkyne 1, 3-dipolar cycloaddition reaction in carbohydrate chemistry," Organic & Biomolecular Chemistry, 2007, vol. 5, Issue 7, pp. 1006-1017.

Dondoni, "Triazole: the Keystone in Glycosylated Molecular Architectures Constructed by a Click Reaction," Chemistry—An Asian Journal, 2007, vol. 2, Issue 6, pp. 700-708.

Zhang et al., "Carbohydrate-Protein Interactions by 'Clicked' Carbohydrate Self-Assembled Monolayers," Analytical Chemistry, 2006, vol. 78, Issue 6, pp. 2001-2008.

Michel et al., "Carbohydrate Microarrays by Microcontact 'Click' Chemistry," Langmuir, 2008, vol. 24, Issue 21, pp. 12116-12118.

Decher et al., "Multilayer Thin Films: Sequential Assembly of Nanocomposite Materials," Wiley-VCH, 2003, ISBN: 3-527-30440-1.

Sanchez et al., "Inhibition of the plasma contact activation system of immobilized heparin: Relation to surface density of functional antithrombin binding sites," Journal of Biomedical Materials Research, 1997, vol. 37, Issue 1, pp. 37-42.

Bronzino, "The Biomedical Engineering Handbook, vol. II," 2000, CRC Press, ISBN: 3-540-66808-X.

Loussouarn et al., "Molecular Basis of Inward Rectification: Structural Features of the Blocker Defined by Extended Polyamine Analogs," Molecular Pharmacology, 2005, vol. 68, Issue 2, pp. 298-304.

Peng et al., "Disulfide Cross-Linked Polyethylenimines (PEI) Prepared via Thiolation of Low Molecular Weight PEI as Highly Efficient Gene Vectors," Bioconjugate Chemistry, 2008, vol. 19, Issue 2, pp. 499-506.

Jonkheijm et al., "Photochemical Surface Patterning by the Thiol-Ene Reaction," Angewandte Chemie, 2008, vol. 47, Issue 23, pp. 4421-4424.

Drumheller et al., "Surface Immobilization of Adhesion Ligands for Investigations of Cell-Substrate Interacting," The Biomedical Engineering Handbook, 2000, vol. 2.

Examination Report issued in Japanese Patent Application No. 2016-124560 dated Jun. 13, 2017.

* cited by examiner

Example 1.1

Example 1.2

Example 1.3

IMMOBILISED BIOLOGICAL ENTITIES

CROSS REFERENCE TO RELATED APPLICATIONS

The present application is a continuation of U.S. Ser. No. 13/911,727, filed on Jun. 6, 2013 which is a division of U.S. Ser. No. 13/045,769, filed on Mar. 11, 2011 which claims the priority of GB Application Serial No. 1004101.0, filed Mar. 12, 2010. The disclosure of the aforementioned applications are incorporated by reference herein in their entireties, and applicants claim the benefits of these applications under 35 U.S.C. § 119.

BACKGROUND OF THE INVENTION

This invention relates to immobilised biological entities, surfaces, and solid objects, for example medical devices, coated with such entities, and processes and intermediates for their production.

When a medical device is placed in the body, or in contact with body fluids, a number of different reactions are set into motion, some of them resulting in the coagulation of the blood in contact with the device surface. In order to counteract this serious adverse effect, the well-known anti-coagulant compound heparin has for a long time been administered systemically to patients before the medical device is placed in their body, or when it is in contact with their body fluids, in order to provide an antithrombotic effect.

Thrombin is one of several coagulation factors, all of which work together to result in the formation of thrombi at a surface in contact with the blood. Antithrombin (also known as antithrombin III) ("AT") is the most prominent coagulation inhibitor. It neutralizes the action of thrombin and other coagulation factors and thus restricts or limits blood coagulation. Heparin dramatically enhances the rate at which antithrombin inhibits coagulation factors.

However, systemic treatment with high doses of heparin is often associated with serious side-effects of which bleeding is the predominant. Another rare, but serious complication of heparin therapy is the development of an allergic response called heparin induced thrombocytopenia that may lead to thrombosis (both venous and arterial). High dose systemic heparin treatment e.g. during surgery also requires frequent monitoring of the activated clotting time (used to monitor and guide heparin therapy) and the corresponding dose adjustments as necessary.

Therefore solutions have been sought where the need for a systemic heparinisation of the patient would be unnecessary or can be limited. It was thought that this could be achieved through a surface modification of the medical devices using the anti-coagulative properties of heparin. Thus a number of more or less successful technologies have been developed where a layer of heparin is attached to the surface of the medical device seeking thereby to render the surface non-thrombogenic. For devices where long term bioactivity is required, heparin should desirably be resistant to leaching and degradation.

Heparin is a polysaccharide carrying negatively charged sulfate and carboxylic acid groups on the saccharide units. Ionic binding of heparin to polycationic surfaces was thus attempted, but these surface modifications suffered from lack of stability resulting in lack of function, as the heparin leached from the surface.

Thereafter different surface modifications have been prepared wherein the heparin has been covalently bound to groups on the surface.

One of the most successful processes for rendering a medical device non-thrombogenic has been the covalent binding of a heparin fragment to a modified surface of the device. The general method and improvements thereof are described in European patents: EP-B-0086186, EP-B-0086187, EP-B-0495820 and U.S. Pat. No. 6,461,665.

These patents describe the preparation of surface modified substrates by first, a selective cleavage of the heparin polysaccharide chain, e.g. using nitrous acid degradation, leading to the formation of terminal aldehyde groups. Secondly, the introduction of one or more surface modifying layers carrying primary amino groups on the surface of the medical device, and thereafter reacting the aldehyde groups on the polysaccharide chain with the amino groups on the surface modifying layers followed by a reduction of the intermediate Schiff's bases to form stable secondary amine bonds.

DE 19604173 relates to medical devices with a polymer surface based on a substituted bis-phenyl monomer to which a pharmaceutically active agent such as heparin may be attached.

WO 2008/090555 relates to a medical device coated with a polymer matrix which incorporates a pharmaceutically active agent. It appears that the active agent may be incorporated within the polymer matrix.

US 2005/0059068 relates to a chemically active surface able to covalently react with substances containing a hydroxyl group and/or an amine group, comprising a solid surface having an activated dendrimer polyamine covalently bonded to said surface through a silane containing reagent, wherein the dendrimer polyamine can covalently bind the substance comprising a hydroxyl group and/or an amine group.

However there is still a requirement for surface modifications that can be performed under mild conditions (e.g. which do not degrade the heparin) which are more easily manipulated, are simpler and more efficient to produce and/or where the bioavailability of the heparin moiety is higher.

Our earlier application WO 2010/029189 relates to a medical device having a coating with an anticoagulant molecule such as heparin covalently attached to the coating via a 1,2,3-triazole linkage. The document describes the azide or alkyne functionalisation of a polyamine; the preparation of alkyne or azide functionalised heparin (both native and nitrous acid degraded heparin); and the reaction to link the derivatised heparin to the derivatised polymer via a 1,2,3-triazole linker.

We have now found a further simple method of covalently attaching entities capable of interacting with mammalian blood to prevent coagulation or thrombus formation, e.g. heparin, and especially full length heparin rather than the degraded heparin of the prior art, to a surface.

SUMMARY OF THE INVENTION

According to the invention we provide, inter alia, a solid object having a surface which comprises an outer coating layer, said outer coating layer being a biocompatible composition comprising a polymer and an anti-coagulant entity capable of interacting with mammalian blood to prevent coagulation or thrombus formation (herein "anti-coagulant entity"), which anti-coagulant entity is covalently attached to said polymer through a linker comprising a thioether. Such solid objects, especially medical devices, are thereby non-thrombogenic.

DETAILED DESCRIPTION OF THE INVENTION

Figure 1:
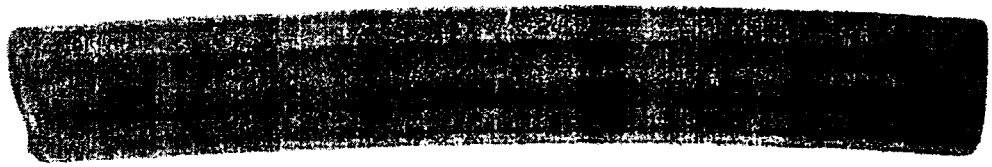
FIG. 1 shows photographs of examples of PVC tubing wherein the luminal side is coated and stained with toluidine blue as described in Examples 1.1-1.3.
Figure 1:
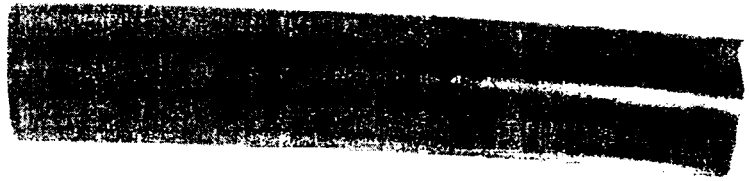
Figure 1:

In general, the outer coating layer comprises a multiplicity of anti-coagulant entities, each of which is covalently attached to the polymer through a linker comprising a thioether.

Anti-coagulant entities are well known to those skilled in the art and many of them are oligosaccharides or polysaccharides. Some of the entities are glycosaminoglycans including compounds containing glucosamine, galactosamine, and/or uronic acid. Among the most suitable glycosaminoglycans are "heparin moieties" and especially full length heparin (i.e. native heparin).

The term "heparin moiety" refers to a heparin molecule, a fragment of the heparin molecule, or a derivative or analogue of heparin. Heparin derivatives can be any functional or structural variation of heparin. Representative variations include alkali metal or alkaline earth metal salts of heparin, such as sodium heparin (e.g. Hepsal or Pularin), potassium heparin (e.g. Clarin), lithium heparin, calcium heparin (e.g. Calciparine), magnesium heparin (e.g. Cutheparine), and low molecular weight heparin (prepared by e.g. oxidative depolymerization or deaminative cleavage, e.g. Ardeparin sodium or Dalteparin). Other examples include heparan sulfate, heparinoids, heparin based compounds and heparin having a hydrophobic counter-ion. Other desirable anti-coagulant entities include synthetic heparin compositions referred to as "fondaparinux" compositions involving antithrombin III-mediated inhibition of factor Xa. Additional derivatives of heparin include heparins and heparin moieties modified by means of e.g. periodate oxidation (U.S. Pat. No. 6,653,457) and other modification reactions know in the art. Heparin moieties also include such moieties bound to a linker or spacer as described below. De-sulphated heparin is less suitable than other forms of heparin because of its reduced non-thrombogenicity relative to other forms of heparin.

Suitably, the anti-coagulant entity is single point attached to the linker, particularly end point attached. When the anti-coagulant entity is an end point attached heparin moiety, it is suitably connected to the linker through its reducing end (sometimes referred to herein as position C1 of the reducing terminal). The advantage of end point attachment, especially reducing end point attachment, is that the biological activity of the anti-coagulant entity (for example the heparin moiety) is maximized due to enhanced availability of the antithrombin interaction sites as compared with attachment elsewhere in the anti-coagulant entity (e.g. heparin moiety).

Where there is a multiplicity of anti-coagulant entities e.g. heparin moieties it is possible for some or all of them to be of a different type; however generally they will all be of the same type.

The term "thioether" refers to a connection between a sulfur and two carbon atoms. This connection is sometimes referred to as "sulfide". The sulphur may be attached to two saturated carbon atoms (i.e. —C—S—C—) or it may be attached to a saturated and an unsaturated carbon atom (i.e. —C—S—C=).

The term "thiol" refers to an —S—H moiety.

The solid object may be any object to which it is desirable to attach anti-coagulant entities. In one embodiment the solid object is a medical device but other solid objects are also contemplated, for example analytical devices and separation devices. Thus, in an alternative embodiment, the solid object is an analytical device or a separation device.

The term "medical device" refers to implantable or non-implantable devices but more usually to implantable medical devices. Examples of implantable medical devices include catheters, stents including bifurcated stents, balloon expandable stents, self-expanding stents, stent-grafts including bifurcated stent-grafts, artificial blood vessels, blood indwelling monitoring devices, artificial heart valves, pacemaker electrodes, guidewires, cardiopulmonary bypass circuits, cannulae, balloons, tissue patch devices and blood pumps. Further examples include grafts including vascular grafts and bifurcated grafts, cardiac leads and drug delivery devices. Examples of or non-implantable medical devices are extracorporeal devices, e.g. extracorporeal blood treatment devices, and transfusion devices.

Medical devices may have neurological, peripheral, cardiac, orthopedal, dermal and gynecological application, inter alia.

An analytical device may be, for example, a solid support for carrying out an analytical process such as chromatography or an immunological assay, reactive chemistry or catalysis. Examples of such devices include slides, beads, well plates, membranes etc. A separation device may be, for example, a solid support for carrying out a separation process such as protein purification, affinity chromatography or ion exchange. Examples of such devices include filters and columns etc.

A medical device may have many coating layers and the term "outer coating layer" refers to a coating layer which, when the device is implanted in a patient, is in contact with the tissues of the patient or is in contact with body fluids. Thus, the outer coating layer may be the coating layer on the outer and/or the inner surface of a hollow device or a device of open structure such as a stent.

Like a medical device, an analytical device or separation device may also have many coating layers and the term "outer coating layer" refers to a coating layer which comes into contact with a substance to be analysed, separated or handled.

At its simplest the linker consists of the thioether only. However more usually the linker comprises at least one spacer in addition to the thioether so that the thioether will be separated by a spacer from either the polymer or the heparin moiety or both.

The Mw (molecular weight) of the linker is suitably from $10^2$ to $10^6$ Da and the length of the linker is suitably from 10 to $10^3$ Å. Suitably, the linkers and/or spacers are straight chain(s), although it is also possible for several, i.e. more than one, e.g. from 2 to 100, preferably 30 to 100 entities (e.g. heparin moieties) to be attached to a single linker thus producing a branched linker in which there are several heparin moiety side chains.

In some embodiments the linker includes one or more aromatic rings. In other embodiments the linker does not include any aromatic rings. In some embodiments the linker is hydrophilic, for example, it may comprise a PEG chain.

In one aspect of the invention, the linker may be formed from multiple portions, for example two, three, four or five portions, more usually three, four or five portions, wherein each portion comprises or consists of a thioether or a spacer.

One example of a three-portion linker comprises "spacer A" between the polymer and the thioether, the thioether itself and "spacer B" between the thioether and the anti-coagulant entity. The molecular weight of spacers A and B may be, for example, between about $10^1$ and $10^3$ Da. In one embodiment, either or both of spacers A and B may comprise an aromatic ring and in an alternative embodiment, neither spacer A nor spacer B comprises an aromatic ring.

In this type of linker, either spacer A or spacer B or both may be a hydrophilic spacer, for example a PEG chain.

As used herein, the term "PEG chain" refers to a polymeric chain obtainable by polymerisation of ethylene oxide, typically of weight between $10^2$ and $10^6$ Da.

In some cases, the linker may comprise two or more thioethers. For example, a bifunctional linker moiety (having, for example an SH group at each end) can be connected at each end, respectively, to an alkyne/alkene functionalized anti-coagulant entity and an alkyne/alkene functionalized polymer resulting in the linker containing two thioethers. Alternatively, use of a bis-alkyne/alkene linker can be connected at each end, respectively, to thiol functionalized anti-coagulant entity and a thiol functionalized polymer also resulting in the linker containing two thioethers.

Linkers having two or more thioethers suitably comprise three, four or five portions where, as set out above, each portion comprises a thioether or a spacer.

In one embodiment, the linker has five portions—"spacer A" between the polymer and a first thioether, the first thioether, "spacer C" between the first thioether and a second thioether, the second thioether, and "spacer B" between the second thioether and the anti-coagulant entity.

In such cases, the molecular weights of spacers A and B may be, for example between about $10^1$ and $10^3$ Da and the molecular weight of spacer C may be between about $10^2$ and $10^6$ Da.

Suitably, one or more of spacer A and/or spacer B and/or spacer C is hydrophilic for example comprising a PEG chain.

In one embodiment, the linker between the anti-coagulant entity such as a heparin moiety and the polymer of the outer coating is an unbranched linker. In another embodiment, the linker between the anti-coagulant entity such as a heparin moiety and the polymer of the outer coating is a branched linker wherein the branch contains another anti-coagulant entity such as a heparin moiety.

The linker can be biodegradable or non-biodegradable but is more suitably non-biodegradable in order that a coated solid object, such as a medical device is non-thrombogenic for a long period of time.

Where there is a multiplicity of linkers it is possible for some or all of them to be of a different type; however suitably all the linkers are of the same type.

In one embodiment, more than one anti-coagulant entity is attached to a linker (e.g. more than one anti-coagulant entity is attached to each linker) (see e.g. Example 1.1). In one embodiment more than one linker is attached to an anti-coagulant entity (e.g. more than one linker is attached to each anti-coagulant entity) (see e.g. Example 1.3).

The surface may comprise a coating layer on a solid object such as a medical device. The solid object may have one or more portions containing void spaces, or pores. The pores may be within the solid object and/or comprising at least one surface of the solid object. An example of a porous solid object is expanded polytetrafluoroethylene (ePTFE).

The solid object, may carry one or more, e.g. 2 or more, or 3 or 4 or 5 e.g. up to 20 coating layers such that desirably a portion of the surface (desired to be non-thrombogenic) or the whole of the surface of the object is covered (Multilayer Thin Films ISBN: 978-3-527-30440-0). The optimum number of layers will depend on the type of material from which the object is made, and the contemplated use of the surface. The surface may, if desired, be made up layer by layer. The number and nature of the layers needed to provide a full coverage of the surface can be easily determined by those skilled in the art. The coating layer(s) may be formed by adsorbing on the surface of the solid object high average molecular weight cationic polymer, e.g. a polyamine (e.g. that known as Polymin available from BASF, see also EP 0086187 Larsson and Gölander) and if needed cross-linking the polyamine with, e.g. an aldehyde crosslinker such as crotonaldehyde and/or glutaraldehyde, followed by the application of a solution of an anionic polymer, e.g. an anionic polysaccharide, e.g. dextran sulfate, to obtain at least one adsorbed layer of the polysaccharide. Hence the surface may comprise a layer of high average molecular weight polyamine and a layer of anionic polysaccharide. More generally, the surface may comprise one or more coating bilayers of cationic polymer (e.g. polyamine) and anionic polymer (e.g. anionic polysaccharide), the innermost layer being a layer of cationic polymer and the outer layer being a layer of cationic polymer to which the anti-coagulant entity is covalently attached via a linker comprising a thioether. This coating procedure is performed essentially as described in EP-B-0495820. Thus it is only the outer coating layer which comprises the anti-coagulant entity. Typically the outer coating layer to which the anti-coagulant entity is attached is not cross-linked.

The procedure of EP-B-0495820 may however be modified so that the outer layer is the anionic polysaccharide which is then reacted, as described below, with a polyamine to which is attached the anti-coagulant entity or a polyamine with functional group(s) capable of forming a linker comprising a thioether.

Prior to applying the first coating layer the surface of the solid object, may be cleaned to improve adhesion and surface coverage. Suitable cleaning agents include solvents as ethanol or isopropanol (IPA), solutions with high pH like solutions comprising a mixture of an alcohol and an aqueous solution of a hydroxide compound (e.g. sodium hydroxide), sodium hydroxide solution as such, solutions containing tetramethyl ammonium hydroxide (TMAH), acidic solutions like Piranha (a mixture of sulfuric acid and hydrogen peroxide), and other oxidizing agents including combinations of sulfuric acid and potassium permanganate or different types of peroxysulfuric acid or peroxydisulfuric acid solutions (also as ammonium, sodium, and potassium salts).

Thus an aspect of the invention is a solid object, for example a medical device having a surface wherein the surface comprises one or more coating bilayers of cationic polymer and anionic polymer, the innermost layer being a layer of cationic polymer and the outermost layer being an outer coating layer of cationic polymer to which an anti-coagulant entity is covalently attached through a linker comprising a thioether.

The polymer of the outer coating layer is typically a polyamine and the outer coating layer may be formed as described above, either by using the procedure described in EP-B-0495820 or a modification of this procedure in which an anionic polymer, typically a polysaccharide, is reacted with a polyamine to which is attached the anti-coagulant entity or a functional group capable of forming a linker comprising a thioether.

Another aspect of the invention is a non-thrombogenic solid object, especially a non-thrombogenic medical device having a surface comprising a functionalized cationic polymer outer coating layer whereby an anti-coagulant entity is attached to the cationic polymer outer coating layer by means of a linker comprising a thioether.

There are a number of ways of forming a thioether but among the most suitable is the reaction of a first compound containing a thiol group with a second compound containing an alkene or an alkyne group. The first and second compounds can each be the polymer of which the outer coating layer is comprised and the anti-coagulant entity as appropriate.

Where the second compound is derivatised with an alkene, in one embodiment an activated alkene is used. An example of a suitable activated alkene is a maleimide derivative.

As noted below, optionally reaction may take place in the presence of a reducing agent such as tris(2-carboxyethyl) phosphine hydrochloride, or alternatively dithiothreitol or sodium borohydride, to avoid or reverse the effective of undesirable coupling of two thiol groups through oxidation.

In one embodiment the reaction is initiated with a radical initiator. An example of a radical initiator is 4,4'-azobis(4-cyanovaleric acid). Further examples are potassium persulfate, 2,2'-azobis[2-(2-imidazolin-2-yl)propane]dihydrochloride and 4-(trimethyl ammoniummethyl) benzophenone chloride.

In another embodiment, the reaction is not initiated with a radical initiator. Instead, conditions of higher pH (e.g. pH 8-11) are used. This type of reaction is more suitable when an activated alkene or alkyne is used for reaction with the thiol.

In general, however, it is preferable to employ acid conditions because these conditions appear most compatible with the heparin and the coating materials.

The reaction between a first compound containing a thiol group and a second compound containing an alkyne group may be represented as follows:

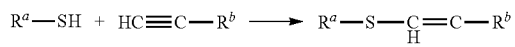

where one of $R^a$ and $R^b$ is the polymer and the other of $R^a$ and $R^b$ is the anti-coagulant entity.

The reaction is described in Example 1.1, where $R^a$ is heparin and $R^b$ is a polyamine and in Example 1.3, where $R^a$ is polyamine and $R^b$ is heparin. The reaction may, for example, be carried out in the presence of tris(2-carboxyethyl)phosphine hydrochloride as reducing agent, and 4,4'-Azobis(4-cyanovaleric acid) as radical initiator, and under acidic conditions.

If an excess of the compound $R^a$—SH is present, there may be further addition across the alkene double bond to produce a compound containing two $R^a$ groups linked to a single $R^b$ group. Again this is illustrated in Example 1.1, where some of the linkers have more than one heparin group attached and in Example 1.3, where some of the heparin is attached to several linkers.

The reaction between a first compound containing a thiol group and a second compound containing a maleimide group may be represented as follows:

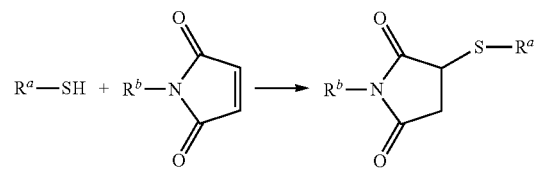

where one of $R^a$ and $R^b$ is the polymer and the other of $R^a$ and $R^b$ is the anti-coagulant entity.

This is described in detail in Example 1.2, where $R^a$ is heparin and $R^b$ is a polyamine. The reaction is generally carried out in the presence of tris(2-carboxyethyl)phosphine hydrochloride as reducing agent, and 4,4'-azobis(4-cyanovaleric acid) as radical initiator, and under acidic conditions.

Another aspect of the invention is a process for preparing a non-thrombogenic solid object, for example a non-thrombogenic medical device, the process comprising:
  (a) treating a solid object such as a medical device to present a surface comprising a cationic polymer outer coating layer which has been functionalized to bear thiol groups;
  (b) reacting said cationic polymer outer coating layer which has been functionalized to bear thiol groups with an anti-coagulant entity which is functionalized to bear an alkene or alkyne group;
  thereby to attach the anti-coagulant entity to the cationic polymer through a linker comprising a thioether.

The invention also provides a solid object, particularly a medical device obtainable by this process.

Another aspect of the invention is a process for preparing a non-thrombogenic solid object, for example a non-thrombogenic medical device, the process comprising:
  (a) treating a solid object such as a medical device to present a cationic polymer outer coating layer which has been functionalized to bear alkene or alkyne groups;
  (b) reacting said cationic polymer outer coating layer which has been functionalized to bear alkyne groups with an anti-coagulant entity which is functionalized to bear a thiol group;
  thereby to attach the anti-coagulant entity to the cationic polymer through a linker comprising a thioether.

The invention also provides a solid object, particularly a medical device obtainable by this process.

Another aspect of the invention is a process for preparing a non-thrombogenic solid object, for example a non-thrombogenic medical device, the process comprising:

(a) treating a solid object such as a medical device to present a cationic polymer surface layer;

(b) associating with said cationic polymer surface layer a functionalized cationic polymer bearing a multiplicity of negatively charged anti-coagulant entities such as heparin moieties which are attached thereto via a linker comprising a thioether said cationic polymer bearing a multiplicity of negatively charged anti-coagulant entities and said functionalized cationic polymer having a net negative charge.

The invention also provides a solid object, particularly a medical device obtainable by this process.

As described above, the cationic polymer surface may be prepared by treating the solid object with a high average molecule weight cationic polymer such as a polyamine and if necessary cross-linking it with e.g. an aldehyde cross-linker. Further layers may optionally be built up by successive steps of (i) application of a solution of anionic polymer (e.g. anionic polysaccharide) to obtain an adsorbed layer of the anionic polymer and (ii) then further treating that with functionalized cationic polymer, such as a polyamine, to provide an adsorbed outer coating layer of functionalized cationic polymer, the outer coating layer being functionalized to bear thiol groups or alkene or alkyne groups.

Typically the first step of treating the object with a high average molecule weight cationic polymer is preceded by the step of cleaning the surface of the object with suitable cleaning agents (e.g. those mentioned above) or other methods of surface pretreatment known in the art to improve adherence and coverage of the first layer e.g. the polyamine layer.

Another aspect of the invention is a process for preparing a non-thrombogenic solid object, for example a non-thrombogenic medical device, the process comprising:

(a) treating a solid object such as a medical device to present an anionic polymer surface layer;

(b) associating with said anionic polymer surface layer a functionalized cationic polymer bearing a multiplicity of negatively charged anti-coagulant entities such as heparin moieties which are attached thereto via a linker comprising a thioether, said functionalized cationic polymer bearing a multiplicity of negatively charged anti-coagulant entities and having a net positive charge.

The invention also provides a solid object, particularly a medical device obtainable by this process.

As described above, the solid object which presents an anionic polymer surface layer is typically prepared by treating the object (e.g. medical device) with a high average molecule weight cationic polymer, such as a polyamine, optionally with cross-linking, followed by treating the polyamine surface with a solution of anionic polymer (e.g. anionic polysaccharide) to obtain an adsorbed outer layer of the anionic polymer. Further layers may be built up by successive steps of (i) application of a cationic polymer (optionally with cross-linking) to provide an adsorbed layer of cationic polymer and (ii) then treating that with a solution of anionic polymer (e.g. anionic polysaccharide) to obtain an adsorbed outer layer of the anionic polymer.

Suitably the anionic polymer is a polysaccharide such as dextran sulfate or a derivative thereof.

As used herein a "polyamine" is a molecule having multiple (e.g. 10, 100, 1000 or more) free pendant amino groups preferably containing at least some primary amino groups. Polyamines are typically polymeric molecules having multiple amino groups of high average molecular weight, for example having an average molecular weight of $10^3$-$10^6$ Da. An exemplary polyamine is a polyethyleneimine such as that known as Polymin available from BASF.

The cationic polymer may be functionalized using techniques known in the art. As illustrated in the Examples below, primary amino groups on the polyamine may be used as points of attachment for the alkene, alkyne or thiol group. However a skilled person would know how to adapt the chemistry to use secondary amino groups on the polyamine as points of attachment for the alkene, alkyne or thiol group. Hence polyamines may be functionalized to bear alkene, alkyne or thiol groups by conventional means e.g. by reacting pendant primary amino groups on the polyamine with an activated carboxylic acid (e.g. an N-hydroxy succinimide derivative of a carboxylic acid) which acid bears an alkene, alkyne or thiol group. Another way is to react secondary amines with carboxylic acids with carbodiimide chemistry or to react with carboxylic acid chlorides where the carboxylic acid portion bears an alkene, alkyne or thiol group.

The anti-coagulant entity, e.g. heparin, carrying an alkene, alkyne or thiol group may be made by conventional methods known per se. For example an anti-coagulant entity, e.g. heparin, carrying an alkyne/alkene group may be made by the reaction of an alkoxyamine of the formula:

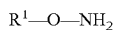

$$R^1\text{—O—NH}_2$$

wherein $R^1$ is an alkyne/alkene-containing group;

with an aldehyde or hemi-acetal group on the anti-coagulant entity using conventional techniques known per se. This type of reaction is illustrated below in Example 3b; the reaction proceeds via formation of an oxy-imine function to give a compound of the formula:

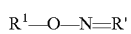

$$R^1\text{—O—N=R'}$$

in which $R^1$ is as defined above and $R'$ is the residue of the anti-coagulant entity.

Nitrous acid degraded heparin and native heparin bear reactive groups, an aldehyde group and a hemi-acetal function respectively, at their reducing end which may be linked in this way.

Similarly, an anti-coagulant entity derivatised with a thiol group may be formed by the reaction of an aldehyde or hemi-acetal group on the anti-coagulant entity with a compound of the formula:

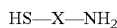

$$\text{HS—X—NH}_2$$

where X is a hydrocarbon linker, for example $(CH_2)_n$ where n is 1 to 8 e.g. 1 to 4, or X is a hydrocarbon linker as just described in which one or more (e.g. 1 or 2) methylene groups are replaced by O; or X comprises a PEG chain containing 1 to 100 (e.g. 1 to 50 such as 1 to 10) ethylene glycol units;

to give a product of the formula

$$R'\text{—CH}_2\text{—NH—X—SH}$$

where X is as defined above and $R'$—$CH_2$— is the residue of the anti-coagulant entity.

An example of such a procedure is given in Example 3a below.

A suitable functional group must also be introduced into the polymer of the outer coating layer so that it can be reacted with the derivatised anti-coagulant entity.

For example, a polyamine polymer bearing a number of primary amine groups represented as follows:

where R" is the polymer residue;
  may be reacted with a compound of the formula:

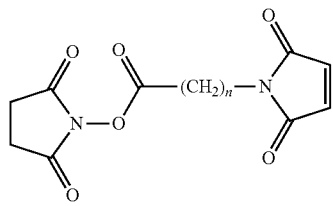

where n is an integer from 1 to 8 e.g. 1 to 4;
  to give a maleimide functionalized polyamine of the formula:

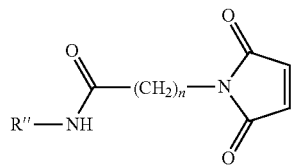

where R" and n are as defined above. This reaction is illustrated in more detail in Example 2a below.

Alternatively, the polyamine polymer may be reacted with an activated alkyne-containing group of the formula:

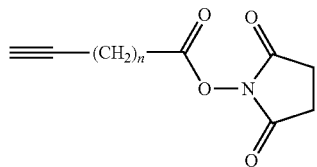

where n is an integer from 1 to 8 e.g. 1 to 4;
  to give an alkyne functionalized polymer of the formula:

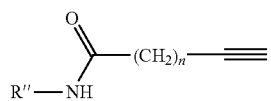

where R" and n are as defined above. This reaction is illustrated in more detail in Example 2b below.

Alternatively, if the polymer is intended to be reacted with an alkene or alkyne-derivatised anti-coagulant entity, it may be derivatised with a thiol group. In this case, a polyamine polymer bearing a number of primary amine groups represented as follows:

where R" is as defined above;
  may be reacted with an activated thiol-containing compound, for example a compound of the formula:

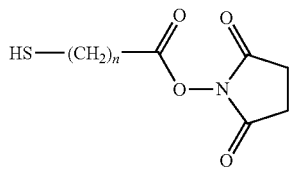

where n is an integer from 1 to 8 e.g. 1 to 4;
  to give a derivatised polymer of the formula:

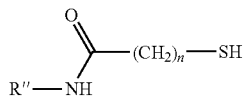

where R" and n are as defined above. This reaction is illustrated in more detail in Example 2c below.

When a coating layer is used, the surface of all and any solid objects is transformed to present the same functionalized outer surface for the subsequent attachment of an anti-coagulant entity capable of interacting with mammalian blood to prevent coagulation or thrombus formation. Hence a specific advantage of the processes described herein is that generally a very uniform non-thrombogenic surface is created (see FIG. 1). This is particularly useful when the solid object is a medical device.

The solid object, e.g. medical device may comprise a metal or a synthetic or naturally occurring organic or inorganic polymer.

Thus, for example, it may be formed from a synthetic or naturally occurring organic or inorganic polymer or material such as polyethylene, polypropylene, polyacrylate, polycarbonate, polyamide, polyurethane (PU), polyvinylchloride (PVC), polyetherketone (PEEK), cellulose, silicone or rubber (polyisoprene), plastics materials, metals, glass, ceramics and other known medical materials or a combination of such materials. Other suitable substrate materials include fluoropolymers, e.g expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), and combinations of the above with and without crosslinking between the polymer chains.

Suitable metals include nickel titanium alloy (Nitinol), stainless steel, titanium, cobalt chromium, gold and platinum. Nitinol and stainless steel are preferred. Titanium is also preferred.

A particularly suitable embodiment of the present invention relates to a coated medical device.

A medical device can be implantable or non-implantable. Examples of implantable or non-implantable medical devices include catheters, stents, stent-grafts, artificial blood vessels, blood indwelling monitoring devices, artificial heart valves, pacemaker electrodes, guidewires, cardiopulmonary bypass circuits, cannulae, balloons, tissue patch devices, blood pumps, and extracorporeal devices, e.g. extracorporeal blood treatment devices, and transfusion devices.

We prefer the coated surface to which the anti-coagulant entity (e.g. heparin or other heparin moiety) is attached to be such that it retains non-thrombogenic properties after sterilization, e.g. ethylene oxide (EO) sterilization.

Sterilization may be carried out by means well known to those skilled in the art. The preferred method of sterilization is using ethylene oxide gas. Alternatively, other methods such as radiation, e.g. e-beam or gamma radiation, may be used where such radiation will not degrade the object or the coating or both.

A preferred embodiment of the present invention relates to a coated medical device for implantation e.g. permanent implantation, or other placement, at an anatomical site. Other preferred embodiments include temporary use devices such as catheters and extracorporeal circuits. Examples are sterile (e.g. sterilized) medical devices for placement inside an anatomical structure delimiting a void space, or lumen, to reinforce the anatomical structure or maintain the void space. Suitably the attached anti-coagulant entity, e.g. heparin or other heparin moiety, does not elute to any substantial extent and remains with the device. For example, after 15 hour rinse with NaCl (0.15 M) prior to testing the retained AT binding activity remains adequate (e.g. greater than 1 or 2 or 4 or 5 or 10 pmol/cm$^2$) and when tested in the Blood loop evaluation test (see Example 1.4) with fresh blood from a healthy donor the reduction in platelet count of the blood after the test is substantially lower for the blood exposed to the coated surface according to the invention than that of an uncoated control (e.g. the reduction in platelet count after the test for the blood exposed to the coated surface is less than 20%, preferably less than 15% and more preferably less than 10%).

Suitably the biocompatible composition of the invention is not biodegradable or bioabsorbable. For biodegradable or bioabsorbable compositions the non-thrombogenic properties may generally be expected to be limited in time.

The non-thrombogenic character of solid objects according to the present invention may be tested by a number of methods. For example non-thrombogenic character may be associated with having a high antithrombin binding activity, especially as compared with solid objects having untreated surfaces.

For example, we prefer the surface, e.g. of the medical device, to have an antithrombin (AT) binding activity of at least 1 e.g. at least 5 picomoles AT per square centimeter (pmol/cm$^2$) of surface. In other embodiments, the AT binding activity is at least 6 pmol/cm$^2$, at least 7 pmol/cm$^2$, at least 8 pmol/cm$^2$, at least 9 pmol/cm$^2$, or at least 10 pmol/cm$^2$ of surface. In some embodiments, the AT binding activity is at least 100 pmol/cm$^2$ of surface. AT binding activity can be measured by methods known in the art, e.g. those described in Pasche., et al., in "Binding of antithrombin to immobilized heparin under varying flow conditions" Artif.-Organs 15:481-491 (1991) and US 2007/0264308. By way of comparison it may be concluded from Sanchez et al (1997) J. Biomed. Mater. Res. 37(1) 37-42, see FIG. 1, that AT binding values of around 2.7-4.8 pmol/cm$^2$ (depending on the experimental set up) or more do not appear to give rise to significant thrombogenic enzymatic activity upon contact with plasma.

Alternatively or additionally we prefer the surface to be non-thrombogenic due to high capacity to suppress coagulation and other defense systems in the Blood loop evaluation test described in Example 1.4. According to that test, the surface to be investigated is applied to a PVC tubing which is rinsed for 15 hours with 0.15M NaCl prior to testing with fresh blood. Non-thrombogenicity is indicated by a reduction in platelet count of the blood measured after the test which is substantially lower for the blood exposed to the surface prepared according the method described herein than that of an uncoated control (e.g. the reduction in platelet count after the test for the blood exposed to the coated surface is less than 20%, preferably less than 15% and more preferably less than 10%).

Other similar blood evaluation methods different from the Blood loop model can be performed by those skilled in the art in order to assess thrombogenicity/non-thrombogenicity.

The amount of the anti-coagulant entity bound to a particular surface area can be controlled and adjusted, e.g. by adjusting the amount of the reagents used in the synthesis of the composition.

The distribution of the anti-coagulant entity on the surface can be determined by conventional staining techniques which are known per se, e.g. the distribution of heparin can be determined using toluidine blue.

According to the invention we also provide a process for the production of a solid object, in particular a medical device, having a surface which comprises an outer coating layer, said outer coating layer being a biocompatible composition comprising a polymer and an anti-coagulant entity capable of interacting with mammalian blood to prevent coagulation or thrombus formation, which anti-coagulant entity is covalently attached to said polymer through a linker comprising a thioether which process comprises the reaction of a corresponding anti-coagulant entity carrying an alkene or alkyne group with a corresponding surface carrying a thiol group, or the reaction of a corresponding anti-coagulant entity carrying a thiol group with a corresponding surface carrying an alkene or alkyne group.

This process may be carried out using procedures known per se.

The surface carrying a thiol group or an alkene or alkyne group may be made by conventional methods known per se, e.g. by reacting a surface, e.g. a surface as described in EP-B-0086186 or EP-B-0086187 carrying negatively charged sulfate groups with an appropriate polyamine carrying either a thiol or an alkene or alkyne group respectively.

According to the invention we also provide a polyamine carrying an anti-coagulant entity through a linker comprising a thioether.

In one embodiment in which the reaction is used the surface carries the thiol group. In another embodiment in which the reaction is used the anti-coagulant entity carries the thiol group.

The reaction may be carried out as described briefly above and in more detail in the Examples below.

By this new method the anti-coagulant entity, e.g. heparin, can advantageously be bound to the surface by surface groups that are not involved in the build up of the surface covering. By contrast, the prior art described in EP-B-0086186, EP-B-0086187 and EP-B-0495820 uses the same type of groups (primary amines) in the layer by layer surface coating process as those used to bind the heparin to the coating.

This new process tends to be less sensitive to pH than are the prior art processes which is also advantageous.

The reaction may also, if desired, be carried out under flow conditions.

According to the invention we also provide an anti-coagulant entity, e.g. heparin or other heparin moiety, which anti-coagulant entity carries an alkene or alkyne or a thiol group. We also provide an anti-coagulant entity, e.g. a heparin moiety capable of interacting with mammalian blood to prevent coagulation or thrombus formation, wherein the anti-coagulant entity carries an alkene or alkyne or a thiol group, which alkene or alkyne or thiol group is attached to a linker, wherein the linker is end-point attached to the anti-coagulant entity (e.g. heparin moiety). When the anti-coagulant entity is a heparin moiety, it may, for example, be a full length heparin moiety (i.e. native heparin).

According to the invention we also provide a functionalized polyamine surface, e.g. a surface prepared essentially as described in EP-B-0086186, EP-B-0086187 and, EP-B-0495820, but additionally carrying one or more thiol or one or more alkene or alkyne groups on the outer coating layer of polyamine.

According to the invention we also provide a solid object, especially a medical device, having a polyamine surface carrying a thiol or an alkene or alkyne group e.g. a thiol or alkene or alkyne group which is connected to an amino group of the polyamine surface via a linker.

According to a further feature of the invention we also provide a process for the production of a solid object, especially a medical device, having a surface which comprises an outer coating layer, said outer coating layer being a biocompatible composition comprising a polymer and an anti-coagulant entity capable of interacting with mammalian blood to prevent coagulation or thrombus formation, which anti-coagulant entity is covalently attached to said polymer through a linker comprising a thioether, wherein the object has a surface which comprises one or more layers of polysaccharide and polyamine, which process comprises the reaction of a corresponding surface having an outer layer of polysaccharide which has a net negative charge (i.e. anionic polysaccharide e.g. carrying negatively charged sulfate groups) with a polyamine, carrying a corresponding anti-coagulant entity through a linker comprising a thioether, having a net positive charge, or the reaction of a corresponding surface having an outer layer of polysaccharide which has a net negative charge (i.e. anionic polysaccharide e.g. carrying negatively charged sulfate groups) with a polyamine carrying a thiol or an alkene or alkyne group which has a net positive charge and reacting the resulting product with an anti-coagulant entity carrying an alkene or alkyne or a thiol group respectively.

References to a polyamine carrying an anti-coagulant entity or a thiol, alkene or alkyne groups include references to a polyamine carrying one or more i.e. a plurality of such groups. However a polyamine carrying a corresponding anti-coagulant entity through a linker comprising a thioether having a net positive charge will only bear so many negatively charged anti-coagulant entities as allows the net charge to remain net positive.

According to a further feature of the invention we also provide a process for the production of a solid object, e.g. a medical device, having a surface which comprises an outer coating layer, said outer coating layer being a biocompatible composition comprising a polymer and an anti-coagulant entity capable of interacting with mammalian blood to prevent coagulation or thrombus formation, which anti-coagulant entity is covalently attached to said polymer through a linker comprising a thioether, wherein the object has a surface which comprises one or more layers of polysaccharide (i.e. anionic polysaccharide e.g. carrying negatively charged sulfate groups) and polyamine, which process comprises the reaction of a corresponding surface having an outer layer of polyamine having a net positive charge with a polyamine carrying a multiplicity of corresponding anti-coagulant entities through a linker comprising a thioether such that said polyamine has a net negative charge.

This process for putting down the layers of polysaccharide and polyamine may be carried out using procedures known per se, for example procedures analogous to those described in EP-B-0495820.

The presence of a net positive charge on a surface may be determined by treatment with Ponceau S which would dye a positively charged surface a red colour.

The presence of a net negative charge on a surface may be determined by treatment with toluidine blue which would dye a negatively charged surface a blue colour.

According to the invention we also provide a functionalized polyamine, e.g. Polymin which carries one or more thiols or one or more alkenes or one or more alkynes e.g. via a linker.

According to the invention we also provide a functionalized polyamine carrying an anti-coagulant entity attached thereto through a linker comprising a thioether. This polyamine may be made by procedures known per se, e.g. analogous to those described elsewhere in this specification.

The products of the invention may have one or more of the following advantageous properties:

The degree of substitution of the anti-coagulant entity on the surface can be controlled;
Both end-point (single point) attachment and multi-point attachment of the anti-coagulant entity, e.g. heparin, can be achieved, although end point (especially reducing end point) attachment is preferred;
The linker length between the anti-coagulant entity and the surface can be controlled;
Full length heparin can be used thus avoiding the cleavage of heparin and the waste of parts of the cleaved product involved in the prior art nitrous acid degradation of heparin;
When cleaving heparin, the antithrombin binding sequence can be destroyed in some of the fragments, therefore using full-length heparin or heparin linked via a spacer can also improve the bioavailability of the bound heparin;
A uniform distribution of the anti-coagulant entity over the surface can be obtained;
A uniform coating may be obtained which will mask the intrinsic properties, for example lower the thromogenic properties, of a device irrespective of the material of its manufacture;
A coating may be obtained which is comparatively smooth;
The biocompatibility of the coating may be enhanced;
A coating according to the present invention may reduce the need for systemic heparin and reduce the likelihood of contact activation;
The bioavailability of the anti-coagulant entity can be controlled, e.g. by the use of different linkers (length, type);
A non-thrombogenic surface which does not leach heparin and therefore has long lifetime can be obtained;
An analytical or separation device with improved binding capacity to biomolecules may be obtained; and
An analytical or separation device with extended heparin activity life time may be obtained.

Other aspects of the invention include a biocompatible composition comprising an anti-coagulant entity capable of interacting with mammalian blood to prevent coagulation or thrombus formation which anti-coagulant entity is covalently attached to a surface through a linker comprising a thioether.

The skilled person will appreciate that the biocompatible composition may be applied to any solid object, of which a medical device is just one example. Therefore according to another aspect of the invention there is provided a solid object having a surface comprising (e.g. coated with) such a biocompatible composition.

The invention is illustrated, but in no way limited, by the following Examples:

EXAMPLE 1.1

Preparation of a Non-Thrombogenic Surface on PVC

A surface comprising layers of aminated polymer and sulfated polysaccharide having a functionalized aminated polymer outer layer is connected to functionalized heparin thereby forming a thioether.

A PVC surface was pretreated using the method described by Larm et al in EP-B-0086186 and EP-495820 (layer-by-layer; polyelectrolyte charge interactions) ending with a layer of sulfated polysaccharide.

The luminal surface of a PVC tubing (I.D. 3 mm) was cleaned with isopropanol and an oxidizing agent. The priming was built-up by alternated adsorption of a positively charged polyamine (Polymin) and negatively charged sulfated polysaccharide (dextran sulfate). The polyamine is crosslinked with a difunctional aldehyde (crotonaldehyde). Every pair of polyamine and sulfated polysaccharide is called one bilayer. The PVC surface was primed with 4 bilayers ending with the sulfated polysaccharide.

Polymin SN (Lupasol SN; Lupasol is an alternative trade name for Polymin) was diluted with water to prepare a stock solution (5 g Polymin SN was added to 20 mL purified water). (Polymin is a polyethyleneimine cationic tenside available from BASF).

1.0 mL of a 5% solution of alkyne functionalized polyamine (preparation see Example 2b) was added to 500 mL of a 0.04 M/0.04 M borate/phosphate buffer at pH 8.0. The adsorption of the alkyne functional polyamine to the sulfate surface was carried out for 20 minutes at room temperature. A two minute water rinse was performed after the adsorption to rinse off excess polymer.

500 mg of nitrite degraded heparin, with thiol functionalization at C1 of the reducing terminal (prepared as in Example 3a), was dissolved in 1000 mL of de-ionized water and 50 mg tris(2-carboxyethyl)phosphine hydrochloride, 500 mg 4,4'-Azobis(4-cyanovaleric acid), and 2.9 g NaCl were added. The pH was adjusted to 3.7 with 1 M HCl (aq).

Figure 2:
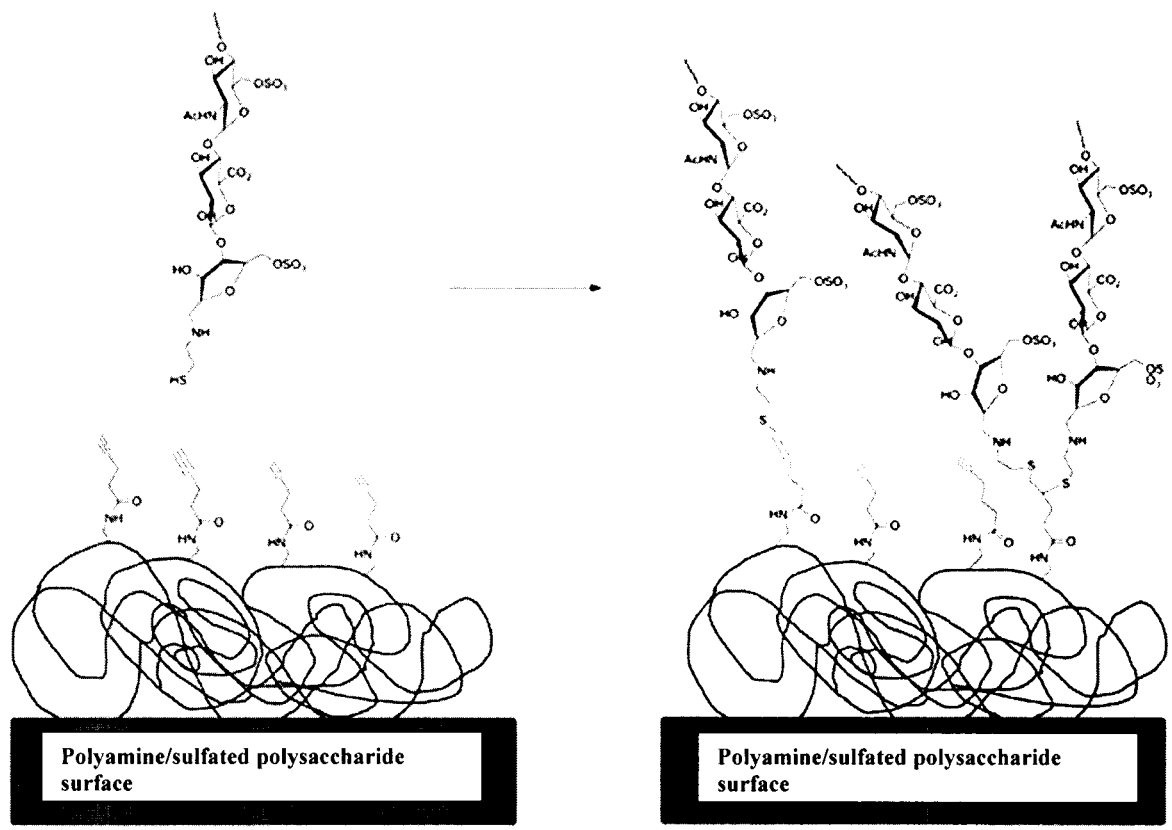
FIG. 2 illustrates the reaction sequence of Example 1.1, in which an alkyne functionalized surface reacts with a thiol functionalized heparin to form a thioether linker.

The reaction between the solution of the thiol functionalized heparin and the alkyne functionalized surface was carried out at 70° C. for 3 h. This reaction sequence is shown in FIG. 2. Purification was performed by rinsing off non-covalently linked heparin for 10 minutes using a 0.04 M/0.04 M borate/phosphate buffer at pH 8.0. A final rinse with de-ionized water for two minutes was performed to wash away buffer salt residues.

The flow used during the entire process was 100 mL/min.

The samples were stained with toluidine blue ("TB") (200 mg/L in water) by immersing in the solution for 2 minutes followed by extensive water rinse. The TB attaches to the heparin via ionic interaction. The samples showed intense uniform stain with TB, see FIG. 1.

Antithrombin binding activity of bound heparin: 2.2 pmol/cm$^2$

The antithrombin binding activity of bound heparin was measured essentially as described in Pasche., et al., in "Binding of antithrombin to immobilized heparin under varying flow conditions" Artif.-Organs 15:481-491 (1991).

Non-thrombogenic as tested by the blood loop—see Example 1.4

EXAMPLE 1.2

Preparation of a Non-Thrombogenic Surface on PVC

The luminal surface of a PVC tubing (internal diameter 3 mm) was cleaned with isopropanol and an oxidizing agent. It was then primed with four bilayers of a positively charged polyamine (Polymin) and a negatively charged sulfated polysaccharide (dextran sulfate) ending with the sulfated polysaccharide.

Then next coating step used a solution of 10 mL of a 1% solution of maleimide functionalized polyamine (prepared as in Example 2a) in 1000 mL of a 0.04 M/0.04 M borate/phosphate buffer at pH 8.0. The adsorption of the maleimide functional polyamine to the sulfate surface was carried out for 20 minutes at room temperature. A two minute water rinse was performed after the adsorption to rinse off excess polymer.

500 mg of nitrite degraded heparin, with thiol functionalization at C1 of the reducing terminal (prepared as in Example 3a), was dissolved in 1000 mL of de-ionized water and 50 mg tris(2-carboxyethyl)phosphine hydrochloride, 500 mg 4,4'-Azobis(4-cyanovaleric acid), and 2.9 g NaCl were added. The pH was adjusted to 3.7 with 1 M HCl (aq).

Figure 3:
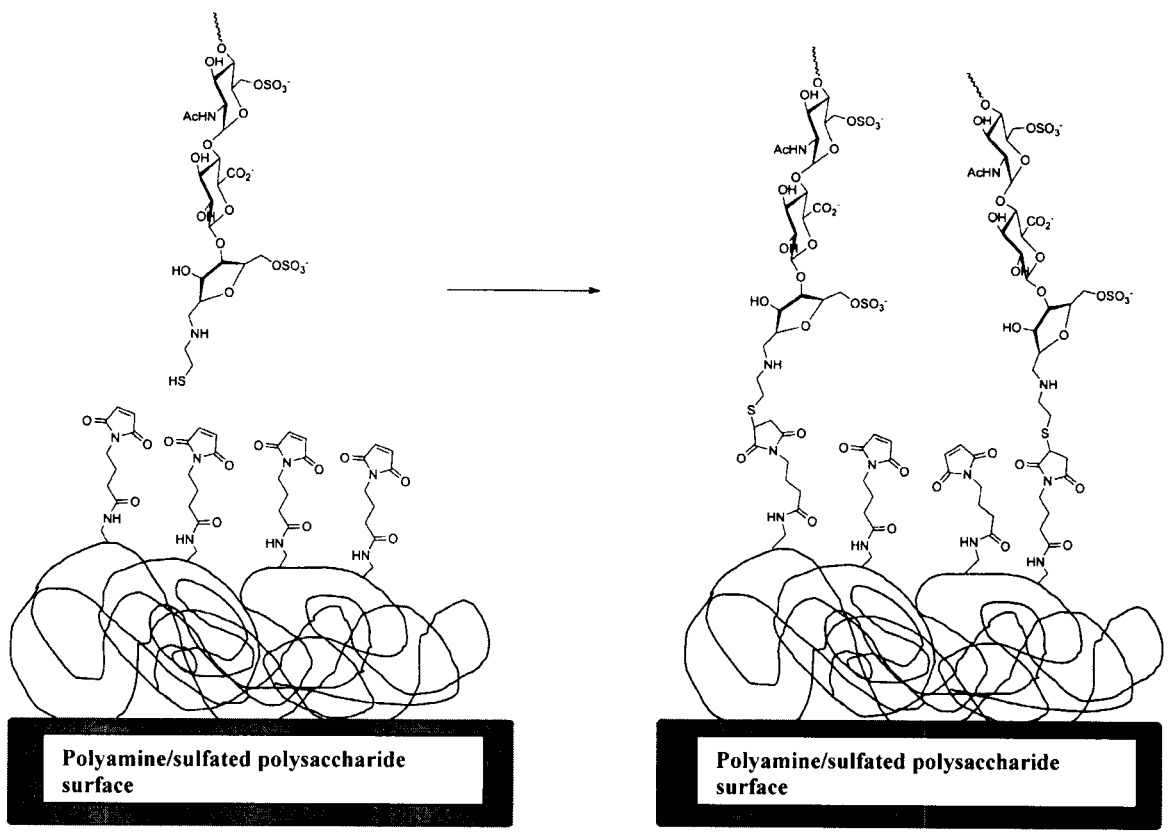
FIG. 3 illustrates the reaction sequence of Example 1.2, in which a maleimide functionalized surface reacts with a thiol functionalized heparin to form a thioether linker.

The reaction between the solution of the thiol functionalized heparin and the maleimide functionalized surface was carried out at 70° C. for 3 h. This reaction sequence is shown in FIG. 3. Purification was performed by rinsing off non-covalently linked heparin for 10 minutes using a 0.04 M/0.04 M borate/phosphate buffer at pH 8.0. A final rinse with de-ionized water for two minutes was performed to wash away buffer salt residues.

The flow used during the entire process was 100 mL/min.

Staining with TB (as described in Example 1.1) showed an intense uniform stain after coating, see FIG. 1.

Antithrombin binding activity of bound heparin: 8.0 pmol/cm$^2$

Non-thrombogenic as tested by the blood loop—see Example 1.4

EXAMPLE 1.3

Preparation of a Non-Thrombogenic Surface on PVC

The luminal surface of a PVC tubing (internal diameter 3 mm) was cleaned with isopropanol and an oxidizing agent. It was then primed with four bilayers of a positively charged polyamine (Polymin) and a negatively charged sulfated polysaccharide (dextran sulfate) ending with the sulfated polysaccharide.

Then next coating step used a solution of 5 mL of a 1% solution of thiol functionalized polyamine (prepared as in Example 2c) and 125 mg of tris(2-carboxyethyl)phosphine hydrochloride in 500 mL of a 0.04 M/0.04 M borate/phosphate buffer at pH 8.0. The adsorption of the thiol functional polyamine to the sulfate surface was carried out for 20 minutes at room temperature. A two minute water rinse was performed after the adsorption to rinse off excess polymer.

250 mg of nitrite degraded heparin, with alkyne functionalization at C1 of the reducing terminal (prepared as in Example 3b), was dissolved in 500 mL of de-ionized water and 25 mg tris(2-carboxyethyl)phosphine hydrochloride, 250 mg 4,4'-Azobis(4-cyanovaleric acid), and 1.4 g NaCl were added. The pH was adjusted to 3.7 with 1 M HCl (aq).

Figure 4:
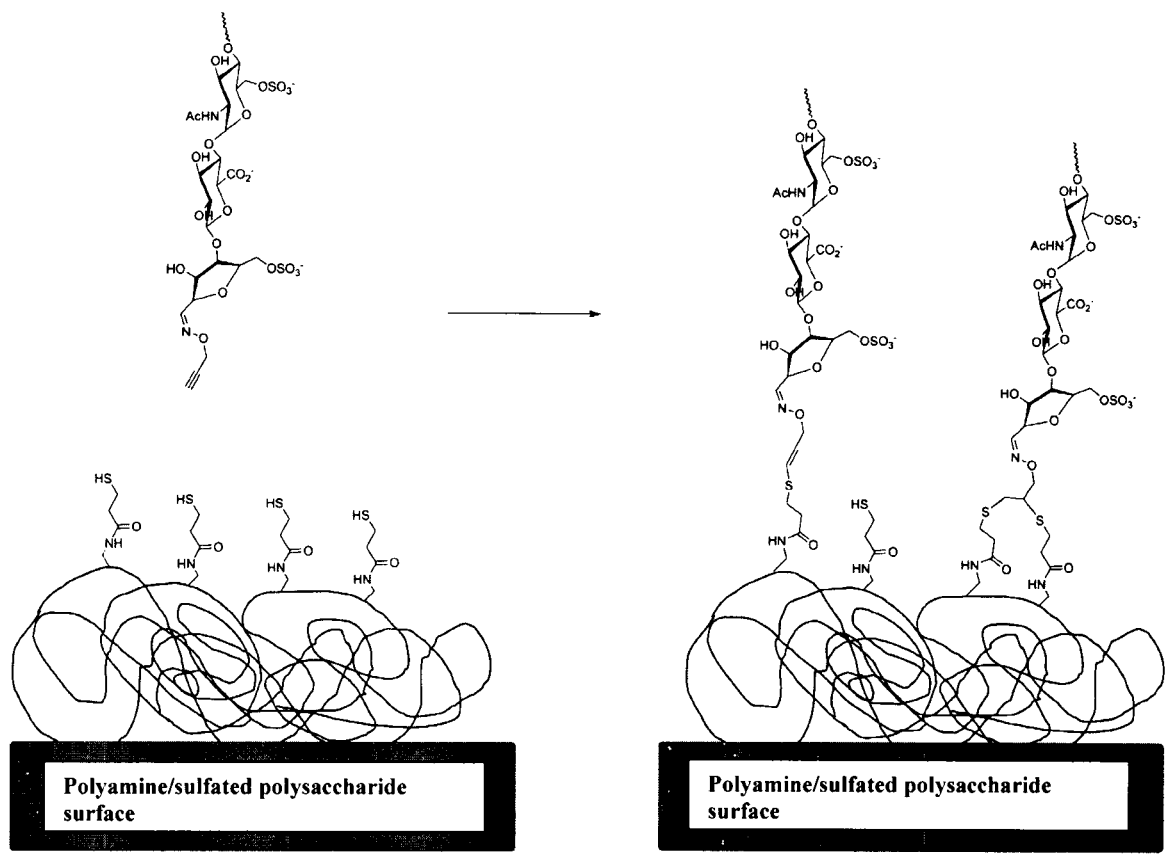
FIG. 4 illustrates the reaction sequence of Example 1.3, in which a thiol functionalized surface reacts with an alkyne functionalized heparin to form a thioether linker.

The reaction between the solution of the alkyne functionalized heparin and the thiol functionalized surface was carried out at 70° C. for 3 h. This reaction sequence is shown in FIG. 4. Purification was performed by rinsing off non-covalently linked heparin for 10 minutes using a 0.04 M/0.04 M borate/phosphate buffer at pH 8.0. A final rinse with de-ionized water for two minutes was performed to wash away buffer salt residues.

The flow used during the entire process was 100 mL/min.

Staining with TB (as described in Example 1.1) showed an intense uniform stain after coating, see FIG. 1.

Antithrombin binding activity of bound heparin: 1.0 pmol/cm$^2$

Non-thrombogenic as tested by the blood loop—see Example 1.4

EXAMPLE 1.4

Blood Loop Evaluation Test

Blood loop evaluation was performed on the luminaly coated PVC tube samples from Examples 1.1-1.3 to show the preserved heparin bioactivity of the non-thrombogenic surface. First the luminal side of the coated tubings were washed with 0.15 M NaCl for 15 hours at a flow of 1 mL/min to ensure that all loosely bound heparin was rinsed off and a stable surface remains. Then the washed tubings were incubated in a Chandler loop model performed essentially according to Anderson et al. (Andersson, J.; Sanchez, J.; Ekdahl, K. N.; Elgue, G.; Nilsson, B.; Larsson, R. J Biomed Mater Res A 2003, 67(2), 458-466) at 20 rpm. The platelets, from fresh blood and from the blood collected from the loops, were counted in a cell counter to measure the loss of platelets which indicates thrombosis. As references were included a non-thrombogenic control (i.e Carmeda® BioActive Surface applied to PVC, which is prepared essentially as described in EP-B-0495820), an uncoated PVC tube, and a thrombogenic control (i.e. a three bilayer coating with an outer layer of sulfated polysaccharide not binding antithrombin).

As seen in the table below, there is virtually no platelet loss (platelet loss indicates thrombosis) seen for the coatings prepared as described in Examples 1.1-1.3. The uncoated PVC tubing and the surface with an outer layer of sulfated polysaccharides (not binding antithrombin) show significant platelet loss in this experiment.

|  | Evaluated surfaces | Platelet count × 10$^9$/L | Loss in platelet count % |
|---|---|---|---|
| Initial value, blood before Chandler loop |  | 202 |  |
| Evaluated surfaces according to the invention | From Example 1.1 | 206 | 0 |
|  | From Example 1.2 | 190 | 6 |
|  | From Example 1.3 | 199 | 1 |
| Reference surfaces | Non-thrombogenic control | 194 | 4 |
|  | Uncoated PVC tube | 57 | 72 |
|  | Thrombogenic control | 9 | 96 |

These results demonstrate the non-thrombogenic properties of the surface prepared according to the invention.

EXAMPLE 2a

Maleimide Functionalization of Polymin SN

Polymin SN (Lupasol SN; Lupasol is an alternative trade name for Polymin) was diluted with water to prepare a stock solution (5 g Polymin SN was added to 20 mL purified water). (Polymin is a polyethyleneimine cationic tenside available from BASF).

4-maleimidobutyric acid (0.50 g, 2.7 mmol) and N-hydroxysuccinimide (NHS) (0.32 g, 2.7 mmol) was dissolved in 3 mL of dichloromethane and stirred at 0° C. A solution of N,N'-dicyclohexylcarbodiimide (0.56 g, 2.7 mmol) in 3 mL of dichloromethane was added slowly to the reaction mixture at 0° C. The reaction mixture was stirred over night and the byproducts were filtered of and the NHS activated 4-maleimidobutyric acid was concentrated and dried under vacuum.

Figure 5:
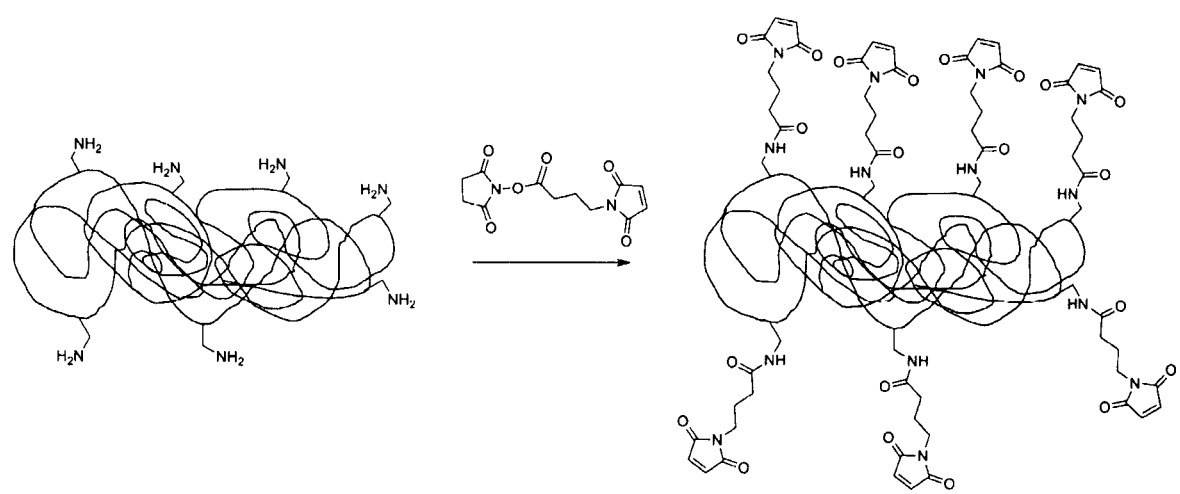
FIG. 5 illustrates the reaction sequence of Example 2a, in which Polymin SN is functionalized with multiple maleimide groups.

The dried NHS activated 4-maleimidobutyric acid was dissolved in 30 mL of purified water and mixed with 7.6 mL of the Polymin SN stock solution at 0° C. and left to react overnight at room temperature to obtain a 1% solution of the maleimide functionalized polymin. This reaction sequence is shown in FIG. 5.

EXAMPLE 2b

Alkyne Functionalization of Polymin SN

Figure 6:
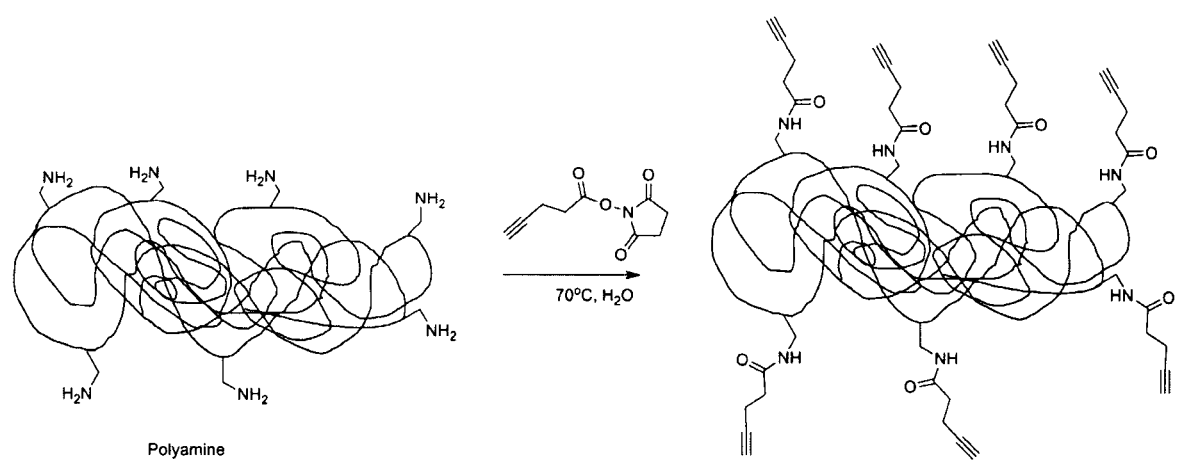
FIG. 6 illustrates the reaction sequence of Example 2b, in which Polymin SN is functionalized with multiple alkyne groups.

A solution of N-hydroxysuccinimide-(4-pentynoate) (Ref: Salmain, M.; Vessieres, A.; Butler, I. S.; Jaouen, G. Bioconjugate Chemistry 1991, 2(1), 13-15) (3.90 g, 19.0 mmol) in 20 mL of purified water was mixed with 24 mL of the Polymin SN stock solution (see example 2a) and left to react overnight at 70° C. This reaction sequence is shown in FIG. 6. The reaction mixture was then diluted with water and isopropanol (min 99%, PhEur quality, Merck) until the polymer precipitated. The isopropanol was decanted off and the residual isopropanol of the resulting slurry was evaporated off.

EXAMPLE 2c

Thiol Functionalization of Polymin SN 3-mercaptopropionic acid (1.00 g, 9.4 mmol) and N-hydroxysuccinimide (NHS) (1.09 g, 9.4 mmol) was dissolved in 1 mL of dichloromethane and stirred at 0° C. under inert atmosphere (Ar).

A solution of N,N'-dicyclohexylcarbodiimide (1.94 g, 9.4 mmol) in 10 mL of dichloromethane was added slowly to the reaction mixture at 0° C. The reaction mixture was stirred over night under inert atmosphere (Ar) at room temperature and the byproducts were filtered of and the NHS activated 3-mercaptopropionic acid was concentrated and dried under vacuum.

Figure 7:
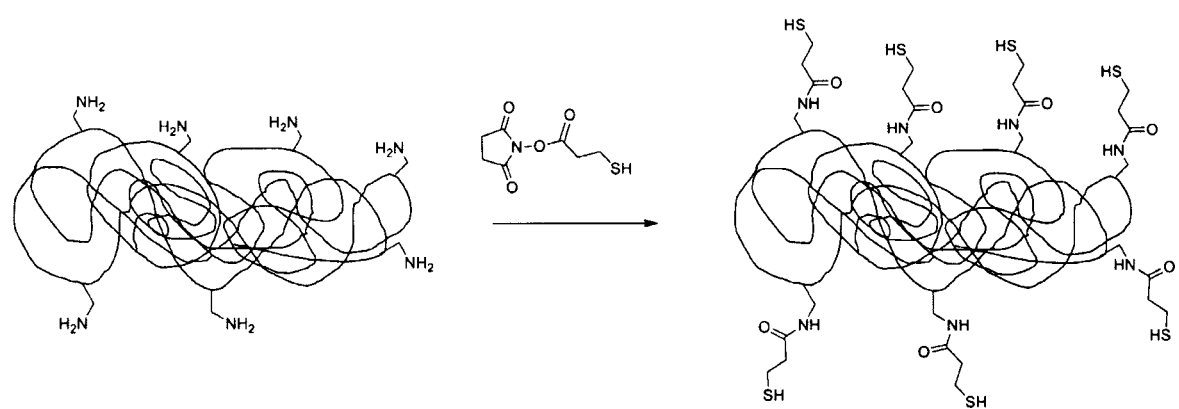
FIG. 7 illustrates the reaction sequence of Example 2c, in which Polymin SN is functionalized with multiple thiol groups.

The dried NHS activated 3-mercaptopropionic acid was dissolved in 115 mL of purified water and mixed with 28.6 mL of the Polymin SN stock solution (see example 2a) at 0° C. and left to react overnight under inert atmosphere (Ar) at room temperature to obtain a 1% solution of the thiol functionalized polymin. This reaction sequence is shown in FIG. 7.

EXAMPLE 3a

Preparation of Thiol Functionalized Nitrous Acid Degraded Heparin

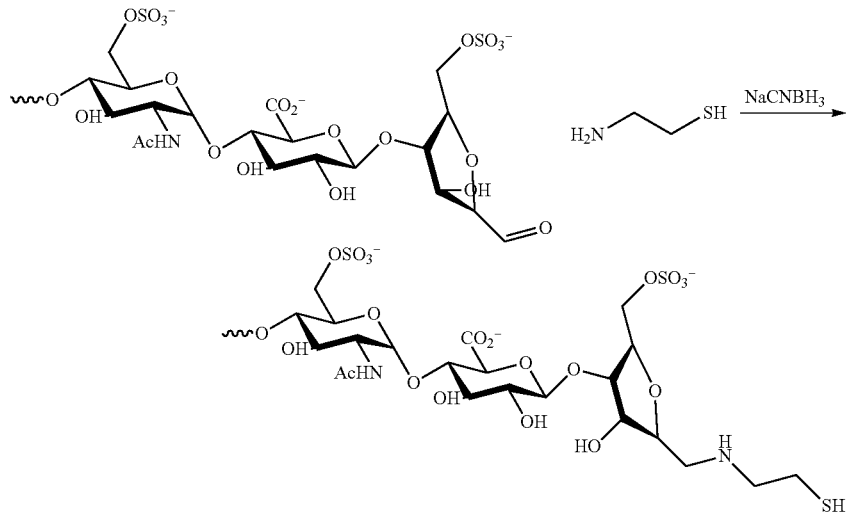

Nitrous acid degraded heparin with aldehyde groups (prepared essentially as in Example 2 of U.S. Pat. No. 4,613,665) (5.00 g, 1.0 mmol), cysteamine hydrochloride (0.57 g, 5.0 mmol) and sodium chloride (0.6 g) were dissolved in purified water. The pH was adjusted to 6.0 with 1 M NaOH (aq) and 1 M HCl (aq). To the solution was added 3.1 ml of 5% (aq) NaCNBH$_3$ (0.16 g, 2.5 mmol) and the reaction was stirred over night at room temperature. The pH was adjusted to 11.0 with 1 M NaOH (aq) and the resulting product was dialyzed against purified water with a SpectraPor dialysis membrane mwco 1kD (flat width 45 mm) for three days. The reaction mixture was then concentrated and freeze dried to obtain 2.6 g of a white fluffy powder.

EXAMPLE 3b

Preparation of Alkyne Functionalized Nitrous Acid Degraded Heparin

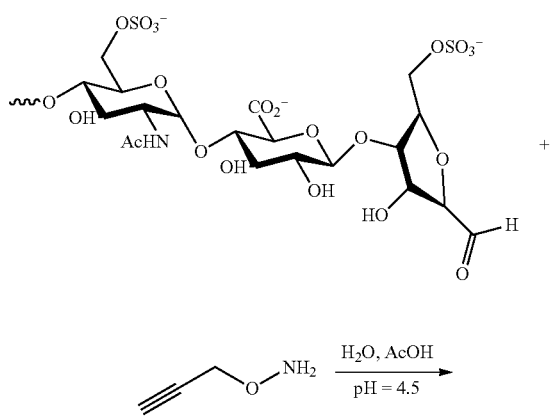

-continued

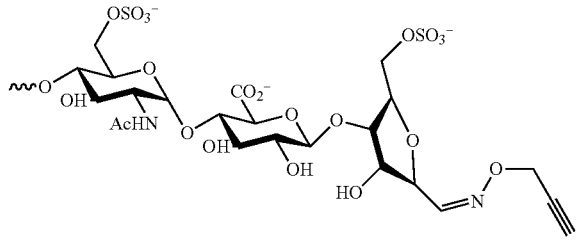

Reagents:

(i) Nitrous acid degraded heparin with aldehyde groups (prepared essentially as in Example 2 of U.S. Pat. No. 4,613,665) 3.25 g dry weight (0.65 mmol)

(ii) O-(prop-2-ynyl)-hydroxylamine hydrochloride (Ref: Xu, R.; Sim, M. K.; Go, M. L., Synthesis and pharmacological characterization of O-alkynyloximes of tropinone and N-methylpiperidinone as muscarinic agonists. *J Med Chem* 1998, 41, (17), 3220-3231) 0.70 g dry weight (6.5 mmol)

(iii) Acetic acid (100% Merck) 3 mL (iv) Purified water 50 mL

The compounds were dissolved in the mixed solvents and the pH adjusted to 4.5 with 4M NaOH. The reaction was continued for 3 days at room temperature. The resulting product was dialyzed against purified water with a SpectraPor dialysis membrane mwco 1 kD (flat width 45 mm). The functionalized product was analyzed by FTIR which showed a typical signal from the alkyne at 3100 cm$^{-1}$.

The activity of the functionalized heparin was 96 IU/mg which indicates that the activity of the functionalized heparin is substantially unaffected by functionalization.

EXAMPLE 3c

Preparation of Alkyne Functionalized Native Heparin

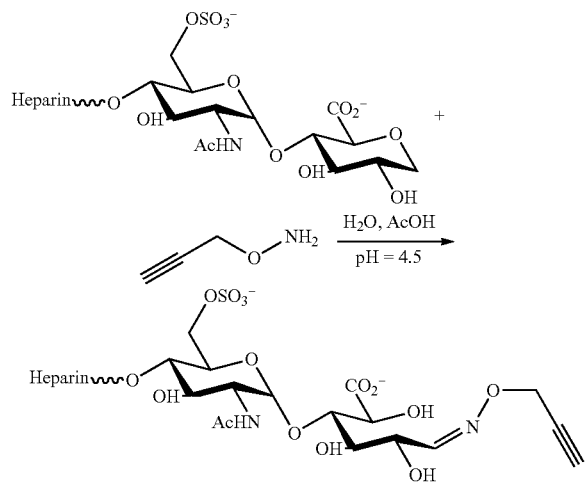

The native heparin (SPL, Scientific Protein Laboratories, lot no. 1037) was functionalized according to the procedures described in Example 3b.

The activity of the functionalized heparin was 211 IU/mg which indicates that the activity of the functionalized heparin is substantially unaffected by functionalization.

EXAMPLE 3d

Preparation of Alkyne Functionalized Native Heparin with Aromatic Spacer

The native heparin (SPL, Scientific Protein Laboratories, lot no. 1037) (20 mg) was dissolved in 250 µL acetic acid (100% Merck) and 250 µL purified water and 6 µL N-(4-(2-(aminoxy)ethyl)phenyl)pent-4-ynamide from stock solution (see Example 5 below) was added. The reaction was carried out at room temperature for 16 hrs. The reaction products were concentrated and co-evaporated with toluene (3×2 mL) to give a yellowish solid (~20 mg).

Preparation of Intermediates

EXAMPLE 5

Bifunctional Linker

5 a) N-(4-(2-(hydroxy)ethyl)phenyl)pent-4-ynamide

N-hydroxysuccinimide-(4-pentynoate) (Ref: Malkoch, M.; Schleicher, K.; Drockenmuller, E.; Hawker, C. J.; Russell, T. P.; Wu, P.; Fokin, V. V., Structurally Diverse Dendritic Libraries: A Highly Efficient Functionalization Approach Using Click Chemistry. *Macromolecules* 2005, 38, (9), 3663-3678.) (200 mg, 1.0 mmol) and p-aminophenylethanol (125 mg, 0.9 mmol) were dissolved in 2 mL of dichloromethane together with triethyl amine (140 µL, 1.0 mmol), and 5 drops of dimethyl formamide. The reaction mixture was stirred at room temperature for 2 hours. The crude reaction product was concentrated, dissolved in 10 mL of ethyl acetate and washed with 5 mL of water followed by, 5 mL of 0.5 M HCl (aq.), 5 mL of 10 NaHCO$_3$ (aq.) and finally 5 mL of water. The organic phase was dried with MgSO$_4$, filtered, and the solvent was evaporated. The product was further purified by column chromatography on silica gel eluting with a gradient of toluene (T) and ethyl acetate

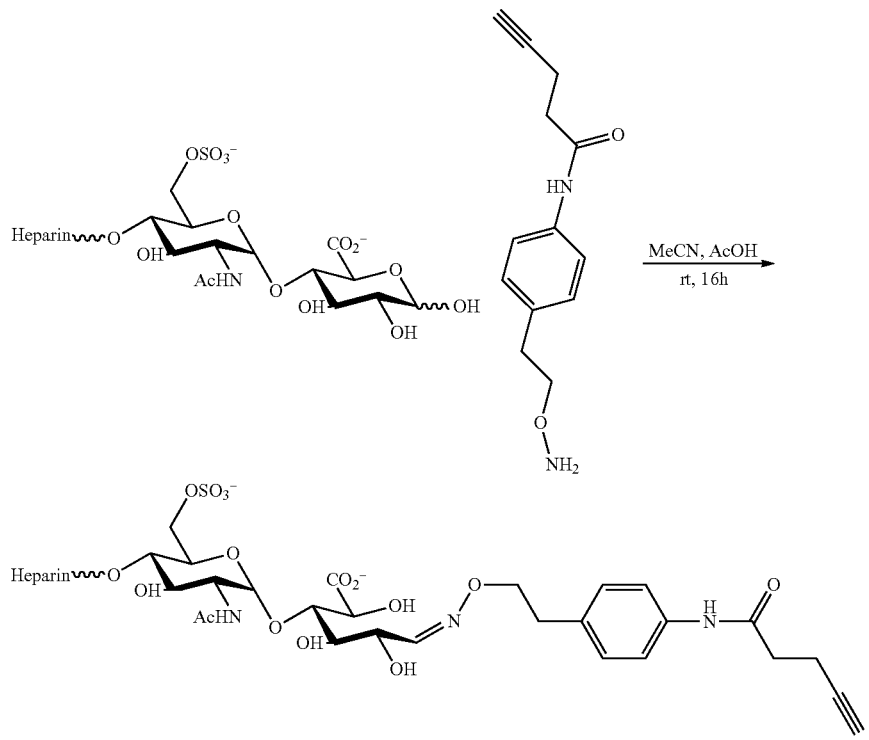

(E) from 4:1 to 1:2 (T:E). The product N-(4-(2-(hydroxy)ethyl)phenyl)pent-4-ynamide was characterized by NMR and MALDI-TOF.

5 b) N-(4-(2-(methanesulfonate)ethyl)phenyl)pent-4-ynamide

N-(4-(2-(hydroxy)ethyl)phenyl)pent-4-ynamide (210 mg, 1.0 mmol) was dissolved in 4 mL of pyridine. Methanesulfonyl chloride (MsCl) (100 µL, 1.3 mmol) was added at 0° C. The stirred reaction was brought back to room temperature and reacted at room temperature for 5 min. The solvent was evaporated and the residue re-dissolved in 10 mL of

5 d) N-(4-(2-(aminoxy)ethyl)phenyl)pent-4-ynamide

N-(4-(2-(N-oxyphthalimide)ethyl)phenyl)pent-4-ynamide (20 mg, 5.5 µmol) and ethylenediamine (200 µL, 3.0 mmol) was dissolved in 2 mL of ethanol. The reaction was stirred at 75° C. for 2 hours. The solvent was evaporated and the crude product purified by column chromatography on silica gel eluting with a gradient of toluene (T) and ethyl acetate(E) from 2:1 to 1:3 (T:E). The product N-(4-(2-(aminoxy)ethyl)phenyl)pent-4-ynamide was characterized by NMR and MALDI-TOF.

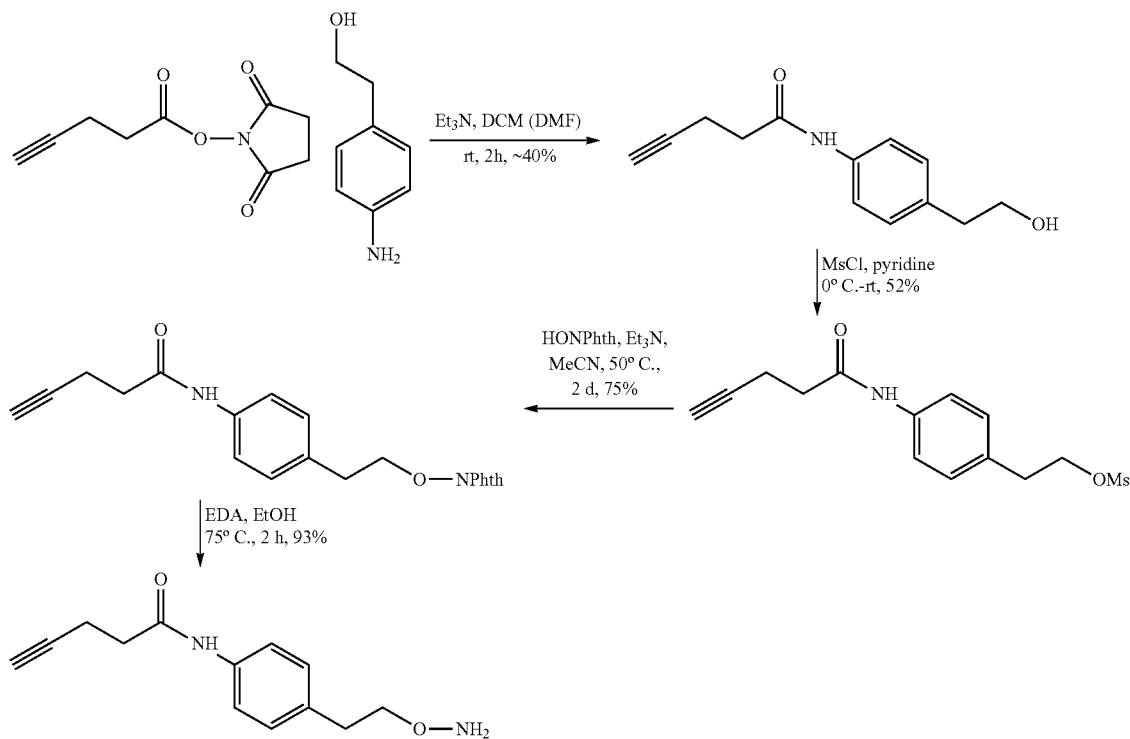

ethyl acetate and washed with 5 mL of water followed by 5 mL of 0.1 M HCl (aq.), and finally 5 mL of water. The organic phase was dried with MgSO₄, filtered, and the solvent was evaporated to yield the product N-(4-(2-(methanesulfonate)ethyl)phenyl)pent-4-ynamide.

5 c) N-(4-(2-(N-oxyphthalimide)ethyl)phenyl)pent-4-ynamide

The N-(4-(2-(methanesulfonate)ethyl)phenyl)pent-4-ynamide was dissolved in 6 mL of acetonitrile and added to a solution of N-hydroxyphthalimide (200 mg, 0.9 mmol) and triethyl amine (250 µl, 1.8 mmol) in 2 mL acetonitrile. The reaction mixture was stirred at 50° C. for 2 days. The reaction mixture was then diluted with 40 mL of ethyl acetate and washed with 20 mL of 0.5 M HCl (aq.), 5×30 mL of 10 NaHCO₃ (aq.) to remove the red color, and finally 5 mL of water. The organic phase was dried with MgSO₄, filtered, and the solvent was evaporated. The crude product was re-crystallized from 10 mL of toluene to obtain N-(4-(2-(N-oxyphthalimide)ethyl)phenyl)pent-4-ynamide which was characterized by NMR and MALDI-TOF.

Preparation of stock solution:

N-(4-(2-(aminoxy)ethyl)phenyl)pent-4-ynamide (2.5 mg) was placed in a metric flask and acetonitrile (1000µL) was added to dissolve the linker.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and suitable and more suitable groups and embodiments of groups recited above.

The invention claimed is:
1. A compound comprising a heparin moiety capable of interacting with mammalian blood to prevent coagulation or thrombus formation which heparin moiety carries an alkene group, which alkene group is directly attached to a linker, wherein the linker is end-point attached to the heparin moiety, wherein the compound is obtainable by reacting an alkene-containing group with an aldehyde group or hemiacetal function at the reducing end of the heparin moiety.

2. The compound according to claim 1 which is a full length heparin.

3. The compound of claim 1, wherein the alkene group is a maleimide derivative.

4. The compound of claim 1, wherein the linker is a thioether.

5. The compound of claim 1, wherein the alkene group is attached to the linker between the heparin moiety and a polymer surface of a medical device.

6. A compound of formula:

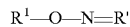

wherein $R^1$ is an alkene-containing group and R' is a heparin moiety bound at its reducing end, capable of interacting with mammalian blood to prevent coagulation or thrombus formation.

7. A heparin moiety capable of interacting with mammalian blood to prevent coagulation or thrombus formation which heparin moiety carries an alkene group comprising a maleimide derivative, which alkene group is attached to a linker, wherein the linker is end-point attached to the heparin moiety.

8. A heparin moiety capable of interacting with mammalian blood to prevent coagulation or thrombus formation which heparin moiety carries an alkene group, which alkene group is attached to a linker comprising a thioether, wherein the linker is end-point attached to the heparin moiety.

* * * * *